United States Patent
Jezek et al.

(10) Patent No.: US 10,925,965 B2
(45) Date of Patent: Feb. 23, 2021

(54) PROTEIN FORMULATIONS WITH INCREASED STABILITY

(75) Inventors: Jan Jezek, Wellingborough (GB); Barry Kingston Derham, Cambridge (GB)

(73) Assignee: Arecor Limited, Cambridge (GB)

( * ) Notice: Subject to any disclaimer, the term of this patent is extended or adjusted under 35 U.S.C. 154(b) by 654 days.

(21) Appl. No.: 13/591,430

(22) Filed: Aug. 22, 2012

(65) Prior Publication Data

US 2013/0149335 A1 Jun. 13, 2013

Related U.S. Application Data

(63) Continuation of application No. PCT/GB2011/050371, filed on Feb. 24, 2011.

(60) Provisional application No. 61/307,528, filed on Feb. 24, 2010.

(51) Int. Cl.
*A61K 47/12* (2006.01)
*A61K 9/00* (2006.01)

(52) U.S. Cl.
CPC ............ *A61K 47/12* (2013.01); *A61K 9/0019* (2013.01)

(58) Field of Classification Search
None
See application file for complete search history.

(56) References Cited

U.S. PATENT DOCUMENTS

| 6,573,237 B2 * | 6/2003 | Rinella, Jr. ............ A61K 38/26 514/356 |
| 2004/0197324 A1 * | 10/2004 | Liu et al. .................... 424/130.1 |
| 2005/0203000 A1 * | 9/2005 | Sutter et al. ........................ 514/3 |
| 2010/0297117 A1 * | 11/2010 | Sloey ...................... A61K 47/22 424/133.1 |

FOREIGN PATENT DOCUMENTS

| EP | 1 800 689 A1 | 6/2007 | |
| WO | WO 2004/091658 A1 | 10/2004 | |
| WO | WO 2005/063298 A1 | 7/2005 | |
| WO | WO 2007/037795 A2 | 4/2007 | |
| WO | WO 2008/084237 * | 7/2008 | ............ A61K 47/18 |
| WO | WO 2009/075859 A2 | 6/2009 | |
| WO | WO 2009/133408 * | 11/2009 | ............... C07K 2/00 |
| WO | WO 2011/104557 A1 | 9/2011 | |

OTHER PUBLICATIONS

Bracci et al., Type I Interferons as vaccine adjuvants against infectious diseases and cancer, Exper Rev. Vaccines, 7(3), 373-381, 2008.*
Swartz et al., Antifungal Properties of Cranberry Juice, Applied Microbiology, Oct. 1968, p. 1524-1527.*
Hirvi et al., The Aroma of Cranberries, Z. Lebensm. Unters. Forsch., 1981, 172:365-367.*
Lakewood, Lakewood Organic Fresh Pressed Juice, Cranberry, Nutrition Info, Webpage, 2015.*
Spectrum, Spectrum Excipients Bulletin, Spectrum Chemical, Aug. 2010.*
Meyer et al, Antimicrobial Preservative Use in Parenteral Products: Past and Present, Journal of Pharmaceutical Sciences, vol. 96, No. 12, Dec. 2007.*
Chipley, John R. "Sodium benzoate and benzoic acid." Antimicrobials in foods 2 (1993): 11-48. (Year: 1993).*
Bean, H. S., "Preservatives for pharmaceuticals," *J. Soc. Cosmet. Chem.*; 23: 703-720; (1972).
Boukarim, C., et al., "Preservatives in Liquid Pharmaceutical Preparations," *The Journal of Applied Research*; 9(1 & 2): 14-17; (2009).
Gupta, S., et al., "Development of a Multidose Formulation for a Humanized Monoclonal Antibody Using Experimental Design Techniques," *AAPS PharmSci*; 5(2): 1-9; (2003).
Maa, Y., et al., "Aggregation of recombinant human growth hormone induced by phenolic compounds," *Intl. J. Pharmaceutics*; 140: 155-168; (1996).
Crowley, M. M., "Chapter 39: Solutions, Emulsions, Suspensions, and Extracts," *Remington: The Science and Practice of Pharmacy; 21st Edition*: 745-749; D.B. Troy (Ed.), Lippincott, Williams & Wilkins (2006).
Remmele, Jr., R. L., et al., "Interleukin-1 Receptor (IL-1R) Liquid Formulation Development Using Differential Scanning Calorimetry," Pharm Res, 15(2):200-208 (1998).

* cited by examiner

*Primary Examiner* — Robert J Yamasaki
(74) *Attorney, Agent, or Firm* — Nixon & Vanderhye P.C.

(57) ABSTRACT

The invention relates to the discovery that the addition of aromatic carboxylate ions inhibit protein instability caused by aromatic preservatives. Thus, the invention relates to compositions, preferably aqueous compositions, comprising a protein, an aromatic preservative and aromatic carboxylate ions. The proteins remain stable and suitable for storage at ambient temperatures or lower, even in aqueous form. Preferably, the aqueous composition comprises a protein, a phenolic preservative and benzoate ions, wherein the pH of the composition is at least 1 unit greater than the $pK_a$ of benzoic acid. The invention also provides methods of reducing protein degradation by aromatic preservatives in an aqueous formulation of a protein susceptible to such degradation, comprising the step of adding aromatic carboxylate ions to the formulation wherein the formulation is maintained at a pH that is at least 1 unit greater than the $pK_a$ of the corresponding aromatic carboxylic acid.

21 Claims, No Drawings

PROTEIN FORMULATIONS WITH INCREASED STABILITY

RELATED APPLICATIONS

This application is a continuation of International Application No. PCT/GB2011/050371, which designated the United States and was filed on Feb. 24, 2011, published in English, which claims the benefit of U.S. Provisional Application No. 61/307,528, filed on Feb. 24, 2010. The entire teachings of the above applications are incorporated herein by reference.

BACKGROUND OF THE INVENTION

Proteins are larger and more complex than traditional organic and inorganic drugs, possessing multiple functional groups in addition to complex three-dimensional structures, and consequently their formulation poses special problems. For a protein to remain biologically active, a formulation must preserve intact the conformational integrity of at least a core sequence of the protein's amino acids while at the same time protecting the protein's multiple functional groups from degradation. Degradation pathways for proteins can involve chemical instability (i.e. any process which involves modification of the protein by bond formation or cleavage resulting in a new chemical entity) or physical instability (i.e. changes in the higher order structure of the protein) Chemical instability can result from deamidation, racemization, hydrolysis, oxidation, beta elimination or disulfide exchange. Physical instability can result from denaturation, aggregation, precipitation or adsorption, for example. Many proteins, for example enzymes, recombinant protein-based vaccines or therapeutic proteins are unstable and are susceptible to structural degradation and consequent loss of activity while stored, particularly in aqueous solutions. The rates of the degradation processes are typically proportional to temperature. Proteins in general and particularly aqueous formulations of proteins are therefore generally more stable at lower temperatures.

Storage considerations of aqueous formulations of proteins may also require that preservatives are present in the formulation to prevent bacterial growth, especially if the finished product containing the formulation is intended for multi-dose therapeutic applications. Most preservatives used to prevent bacterial growth in protein containing pharmaceutical formulations are not compatible with protein formulations. The list of preservatives available to the protein formulation scientist quickly narrows to just a few compounds. Thirmerosal, an aromatic organomercury compound, has been used since 1930s as a preservative in a number of biological and drug products, particularly vaccines. Nowadays, the use of thimerosal is limited to several vaccines and, due to safety concerns, its future use is likely to be very limited.

Preservatives that have been approved by regulatory authorities for other mufti-dose therapeutic applications include compounds such as benzalkonium salts and aromatic alcohols such as phenol, benzyl alcohol, parabens such as methyl or propyl paraben, catechol, resorcinol and m-cresol. Phenol, m-cresol and benzyl alcohol are generally preferred in currently marketed multi-dose protein-based biologics.

Benzoic acid inhibits the growth of mold, yeast and some bacteria, and has been used as a preservative in various food products. It has also been used as an antifungal agent in topical applications. The efficacy of antimicrobial power of benzoic add is known to decrease significantly at pH>4.5 (http://www.nysaes.cornell.edu/necfe/pubs/pdf/Venture/venture2_chemical.html) due to dissociation of the carboxylate group.

In screening preservatives for use in formulations it is necessary to determine what levels of preservatives are efficacious at preventing bacterial growth in the particular formulation while maintaining the integrity of the protein as well as the integrity of the preservative in combination with the other excipients in the protein formulation. The efficacy of the preservative is dependent on the other excipients in the formulation hence the formulation scientist must assess the final formulations conditions in a preservative challenge test which complies with the Pharmacopoeia Antimicrobial Effectiveness Test (USP <51>, Vol. 32).

Proteins are generally not exceedingly stable in the presence of preservatives. The preferred preservatives typically comprise a hydrophobic region, such as a benzene ring, that may interact with hydrophobic regions of the protein leading to a disruption in protein structure.

Therefore, aqueous protein formulations having improved protein stability at ambient temperatures or lower temperatures in the presence of a preservative, particularly an aromatic preservative, such as phenol or m-cresol, are needed.

SUMMARY OF THE INVENTION

The invention relates to the discovery that the addition of aromatic carboxylate ions, such as benzoate ions, inhibits protein instability caused by phenolic preservatives. Such instability may manifest itself, e.g., by generation of breakdown products or generation of high molecular weight species which is evidence of aggregation. Thus, the invention relates to aqueous compositions comprising a protein, an aromatic preservative and aromatic carboxylate ions, such as benzoate ions. The proteins remain stable and suitable for storage at ambient temperatures or lower, even in aqueous form. Preferably, the aqueous composition comprises a protein, a phenolic preservative and benzoate ions, wherein the pH of the composition is at least 1 unit greater than the pKa of benzoic acid. The invention also provides methods of reducing protein degradation by phenolics in an aqueous formulation of a protein susceptible to such phenolic degradation, comprising the step of adding aromatic carboxylate ions e.g. benzoate ions to the formulation wherein the formulation is maintained at a pH that is at least 1 unit greater than the pKa of benzoic acid.

DETAILED DESCRIPTION OF THE INVENTION

Accordingly, the aqueous protein formulations of the present invention comprise benzoate ions or other aromatic carboxylate ions and have improved stability in the presence of aromatic preservatives.

As used herein, "preservative" is a compound which can be added to an aqueous protein formulation to essentially reduce microbial (e.g., bacterial) action. "Preservative" can also mean a combination of such compounds e.g. a pair of such compounds. Examples of potential aromatic preservatives include aromatic alcohols (i.e. substances containing both an aromatic ring and an alcohol function, not necessarily directly connected) such as phenol, benzyl alcohol, parabens such as methyl or propyl paraben, catechol, resorcinol, m-cresol and chlorocresol, preferably phenol, m-cresol and benzyl alcohol. "Parabens" are carboxylic acid esters of 4-hydroxybenzoic acid. For example the aromatic alcohol may contain a hydroxyl function directly attached to an aromatic ring. Aromatic rings include carbocyclic aromatic rings such as phenyl and naphthyl rings and heterocyclic aromatic rings such as 5-10 membered heteroaromatic rings containing one or more (e.g. 1 to 3) heteroatoms selected from N, O and S, especially N and O particularly O. Aromatic preservatives should not contain a carboxylic acid function.

A sub-class of aromatic alcohol preservatives are phenolic preservatives such as phenol or derivatives of phenol (i.e. they include at least a phenyl ring with —OH attached). A second sub-class of aromatic alcohol preservatives are benzylic alcohols, such as benzyl alcohol or derivatives of benzyl alcohol. The invention is in part based on the discovery that aromatic preservatives can cause protein degradation, particularly degradation of proteins with exposed hydrophobic surfaces. The invention is further based on the discovery that the addition of aromatic carboxylate ions, such as benzoate ions, reduces this degradation. Protein stability is further enhanced or optimized in the presence of aromatic carboxylate ions and especially benzoate ions when the pH of the formulation is at least about 5.2, preferably at least about 5.5, 6, 6.5 or 7. Suitably the pH is about 8.5 or less e.g. 8.0 or less. Thus most suitable pH ranges include, for example, 6 to 8.5 e.g. 6.5 to 8.0. It is noted that the pKa of benzoic acid is around 4.2. In maintaining the pH at least about one unit Greater than the pKa of the aromatic carboxylic acid such as benzoic acid, protein degradation by the phenolic preservatives is substantially reduced. Suitably the pH is less than around 5 e.g. less than around 4 pH units higher than the pKa of the aromatic carboxylic acid.

The aromatic carboxylic acid ions e.g. the benzoate ions are added in an amount effective to reduce phenolic degradation.

As used herein reference to a particular "aromatic carboxylate" e.g. "benzoate" includes reference to a corresponding aromatic carboxylic acid e.g. benzoic acid and vice versa, the species present in the composition (i.e. acid or anion) being determined by the pH.

A range of low molecular weight compounds can be used instead of benzoate. Examples of such compounds include substituted benzoates and benzoate homologues with small bridging groups between the aromatic ring and the carboxylate Group. Substituted benzoates may be selected from compounds bearing one or more substitutents on other positions of the benzene ring. Benzoate homologues include compounds in which the carboxylate group is associated (i.e. directly or indirectly connected) to a fused aromatic ring system, such as naphthalene, as in the case of 1-naphthoic acid and 2-naphthoic acid. A further example is xinafoate (1-hydroxy-2-naphthoate).

Aromatic carboxylic acids include compounds in which a carboxylic acid function is associated (i.e. directly connected or indirectly connected via a small bridging group) to an aromatic ring. Aromatic rings include carbocyclic aromatic rings such as phenyl and naphthyl rings and heterocyclic aromatic rings such as 5-10 membered heteroaromatic rings containing one or more (e.g. 1 to 3) heteroatoms selected from N, O and S, especially N and O particularly O.

The most suitable aromatic ring is phenyl.

Thus benzoate homologues may also be selected from compounds in which there is a bridging group between the aromatic ring and the carboxylate group which comprises one or two carbon atoms, optionally substituted with oxygen-containing functional groups (e.g. hydroxy) and in the case of a two-carbon linker, this may be saturated or unsaturated. Such benzoate homologues may, for example, be selected from phenylacetic acid, mandelic acid, 2-phenylpropanoic acid, phenyl lactic acid and cinnamic acid. Preferably, these low molecular weight compounds are used at a pH at which the ionizable carboxylic acid group is at least 90% ionized, i.e. at a pH at least one unit higher than the pKa of the carboxylate group of the aromatic carboxylic acid.

Suitably the aromatic carboxylic acid is not an aromatic amino acid.

In certain embodiments the aromatic carboxylic acid comprises two or more (e.g. two) carboxylic acid groups as in phthalic acid.

Where the aromatic carboxylic acid bears more than one carboxylate group, as used herein, references to the pKa of said aromatic carboxylic acid are to be read as references to the lowest pKa of any carboxylic acid group of said aromatic carboxylic acid.

Suitably the aromatic carboxylic acid bears a single carboxylate group.

In certain embodiments a mixture of two or more aromatic carboxylic acids are used, for example a mixture of benzoic acid and phenylacetic acid.

A list of exemplary aromatic carboxylic acids is given in Table A below:

TABLE A

| COMPOUND (as acid) | pKa value(s) of carboxylate group(s) |
|---|---|
| Benzoic acid | 4.17 |
| 2-hydroxybenzoic acid (salicylic acid) | 2.98 |
| 3-hydroxybenzoic acid | 4.08 |
| 4-hydroxybenzoic acid | 4.58 |
| 3,4,5-trihydroxybenzoic acid (gallic acid) | 4.41 |
| 4-hydroxy-3-methoxybenzoic acid (vanillic acid) | 4.5 |
| phthalic acid (1,2) | 2.98, 5.28 |
| isophthalic acid (1,3) | 3.46, 4.46 |
| terephthalic acid (1,4) | 3.46, 4.46 |
| 1-naphthoic acid | 3.70 |
| 2-naphthoic acid | 4.17 |
| indole-3-acetic acid | 4.75 |
| phenylacetic acid | 4.28 |
| 3-phenylpropionic acid | 4.66 |
| trans-cinnamic acid | 4.44 |
| cis-cinnamic acid | 3.89 |
| mandelic acid | 3.85 |

The amount of the aromatic carboxylic acid present in the aqueous protein formulation can vary, and may be at a molar concentration that is lower, higher or approximately the same as that of the aromatic preservative. In the case of an individual compound, the amount present may be determined by its maximum solubility in the aqueous medium at the desired storage temperature and pH.

The molar concentration of the aromatic carboxylate ions, for example of benzoate ions, can be at least about 1 mM e.g. in the range of 1-500 mM, preferably 1-200 mM, more preferable 5-100 mM or 5-50 mM, such as a molar concentration of 5 mM, 10 mM or 20 mM.

Similarly the amount of aromatic preservative present in the aqueous protein formulations can vary. The molar concentration of the aromatic preservative, for example of phenol, can be in the range of 5-100 mM, preferably 10-60 mM, more preferably 20-40 mM such as molar concentrations of 20 mM or 30 mM. A person skilled in the art may determine the amount of preservative required in a particular formulation based on the outcome of a preservative challenge test which complies with the Pharmacopoeia Antimicrobial Effectiveness Test (USP <51>, Vol. 32).

The invention is applicable to any protein (as described below) used in human or animal therapy that requires a multi-dose administration and the presence of an aromatic preservative. The protein concentration in compositions for therapeutic or prophylactic use varies across a wide concentration range, from approximately 1 µg/ml to approximately 100 mg/ml, depending on the indication and the nature of the therapeutic product. In addition, multi-dose subcutaneous administration of therapeutic proteins may require concentrations higher than 100 mg/ml, such as 150 mg/ml, 200 mg/ml or 300 mg/ml. The present invention is applicable across the entire range of protein concentrations between approximately 1 µg/ml to approximately 300 mg/ml.

The term "protein" is used herein to include molecules or molecular complexes having an amino acid sequence of sufficient chain length to produce a secondary structure and includes single polypeptide chains or protein complexes comprising two or more polypeptides. The term "protein" is intended to encompass molecules optionally comprising covalently linked non-amino acid moieties such as glycosylated peptides, lipoproteins, pegylated, or conjugated proteins. Included in the term "protein" are metalloproteins having a particular three dimensional structure and a biological activity of interest in which activity and/or structure are dependent on retention of a particular metal on in a binding site within the protein. The metal may be bound directly to the amino acid side chains of the protein or it can be part of a more complex chemical component which is bound within the protein structure. Also included in the term "protein" are protein-based supramolecular systems, defined as systems made up of a discrete number of assembled molecular subunits or components, Examples of such supramolecular systems include protein multimers, virus-like particles and inactivated or attenuated viruses.

The proteins used in the claimed invention are preferably those intended for multi-dose applications, such as in multi-dose vials, injection pens, pumps and other devices. Preservative is an essential component in such applications.

The proteins used in the claimed invention preferably have a phenol attracting region. Such proteins can be identified or characterized by a hydrophobic surface or accessible domain or region.

Examples of proteins used in the claimed invention include: protein or peptide hormones and growth factors, such as: Insulin, Glucagon, Human growth hormone, Gonadotropin, Human thyroid stimulation hormone, Granulocyte colony stimulation factor, Parathyroid hormone, Calcitonin and Erythropoietin and also Somatropin; therapeutic enzymes such as, Streptokinase, Asparaginase, and Urate oxidase; vaccines, including recombinant protein vaccines.

The invention may also be employed to improve the stability of the protein content of vaccines generally such as inactivated or attenuated viruses or whole ceil vaccines, such as vaccines for Hepatitis B, Haemophilus influenza, Diphtheria, Malaria, Human papilloma, Meningitis A, Meningitis C, Pertussis, Polio. Further example vaccines include those for Hepatitis A, Cholera, Pneumonia and Typhoid.

Examples of other proteins used in the claimed invention include therapeutic antibodies, immunoglobulins, fusion proteins, interferons, including interferon alpha, interferon beta and interferon gammablood coagulation factors, such as Factor VIII and Factor IX and Factor VIIa, and antimicrobial peptides such as Caspofungin.

The invention is also applicable enzymes such as uricase and horseradish peroxidase in compositions for therapeutic or diagnostic applications.

It will be understood that whilst the above examples represent the preferred types of proteins used in the claimed invention, the invention is applicable to any protein or protein-containing system formulated in the presence of a preservative, particularly any such protein which is prone to or shows signs of destabilization in the presence of preservatives. Such signs of destabilization may for example be evident from loss of protein activity following incubation of the preservative-containing formulation, relative to a control formulation not containing the preservative.

The protein is present at a concentration intended to achieve its therapeutic effect or another essential function. Preferably, the composition according to all aspects of the present invention comprise a pharmacologically acceptable surfactant such as polysorbate 20, polysorbate 40, polysorbate 60, polysorbate 80, poloxamer 188 or poloxamer 407.

Preferably, the osmolarity of the composition according to all aspects of the present invention is between 150 500 mOsm/L, more preferably between 220-380 mOsm/L, most preferably around 300 mOsm/L.

Preferably, the composition according to all aspects of the present invention is sterile, the sterility being achieved by filtering the composition prior to the final filling to an appropriate container, such as a vial or a pre-filled syringe, under sterile conditions, using an appropriate filter or membrane, such as a0.22 µm filter.

The compositions according to the present invention may contain other components, such as a chelating agent to complex metals or a protease inhibitor to ensure that the protein is not slowly digested by protease activity present in the sample. Another additive that may be used is a polyalcohol e.g. at a concentration of at least 0.5%, and typically up to 5% (w/w). Examples of such compounds are saccharides such as sucrose or trehalose or sugar alcohols such as inositol, lactitol, mannitol or xylitol. Further examples of polyalcohols include 1,2-propanediol, glycerol, sorbitol and raffinose. 1,2-Propanediol and mannitol are preferred polyalcohols.

The invention is applicable to proteins dissolved freely in aqueous solutions or aqueous gel forms or to proteins present in an aqueous system as a dispersion or suspension, as well as proteins attached to solid substrates such as vaccine adjuvant or cellular membrane by means of hydrophobic, ionic or ligand exchange interactions. The invention is also applicable to proteins in solid state where water has been removed partially or fully from an aqueous solution by drying or by freeze-drying or by spray-drying where free or bound water is still present.

Thus according to the invention there is provided a method which comprises partially or fully removing water from an aqueous solution according to the invention; there is also provided the product of such a method.

A "stable" formulation is one in which the protein therein substantially retains its physical and chemical stability and integrity upon storage. "Improved stability" as used herein means that a protein formulation is more stable in the presence of a preservative and aromatic benzoate ions as compared to the same protein formulation in the presence of the preservative alone under the same conditions of testing.

Various analytical techniques for measuring protein stability are available in the art (see, for example, Herron J. N., Jiskoot W. and Crommelin J. A. (Eds.) *Physical Methods to*

*Characterize Pharmaceutical Proteins*, Plenum Press, New York/London, 1995). Stability can be measured at a selected temperature for a selected time period. Whilst storage stability at 2-8° C. and 2.5° C. is typically of practical importance, storage under accelerated stress conditions, such as at 40° C. or at 60° C., can be used to assess the stability of the protein. Formulations of the invention have improved stability upon storage at temperatures ranging from refrigeration temperatures to room temperature for at least 1 month, preferably for at least 13 weeks. In a preferred embodiment thereof, such formulations have improved stability upon storage at temperatures between 2° C. and 8° C. for several months, e.g. for 3 months, preferably for at least 12 months, most preferably for at least 18 months. In one preferred embodiment thereof, such formulations have improved stability at temperatures between 15° C. and 25° C. for at least 13 weeks. In another preferred embodiment, the composition is storage stable at 25° C. for a minimum of 18 weeks. In another embodiment the composition is storage stable at 5 C for a minimum of 26 weeks and preferably at least 52 weeks.

As discussed above, benzoate ions, the preferred stabilizer according to the present invention, is preferably used at a pH greater than about 5.2. Buffers, particularly displaced buffers, can be used to control and maintain the pH. Displaced buffers are described, for example, in WO2008084327A2, which is incorporated herein by reference. In a particularly preferred embodiment, a displaced buffer system comprising benzoate and a second buffer is selected. The second buffer is preferably selected from the group consisting of TRIS, glycine, arginine and methionine.

In a displaced buffer system, it is typically preferred to avoid using an ionizable species that has a pKa within 1 pH unit of the selected pH. Such displaced buffers are suitably present in an amount such that the molarity of each buffer is at least 1 mM and/or less than 1 M, preferably 2 mM to 200 mM, most preferably 5 mM to 100 mM. In one embodiment, one or more displaced buffers are preferably present at a concentration of 1 mM to about 1M; more preferably at a concentration of from about 2 mM to about 200 mM, and even more preferably at a concentration from about 5 mM to about 100 mM.

Thus in one embodiment the protein composition of the invention comprises two displacement buffers comprising at least one displacement buffer having a $pK_a$ that is at least 1 unit greater than the pH of the composition at the desired temperature and at least one displacement buffer (preferably, benzoate) having a $pK_a$ that is at least 1 unit less than the pH of the composition at the desired temperature. In one embodiment the protein composition of the invention comprises two displacement buffers comprising at least one displacement buffer having a $pK_a$ that is at least 1.5 units greater than the pH of the composition at the desired temperature and at least one displacement buffer having a $pK_a$ that is at least 1.5 units less than the pH of the composition at the desired temperature. In one embodiment the protein composition of the invention comprises two displacement buffers comprising at least one displacement buffer having a $pK_a$ that is at least 2 units greater than the pH of the composition at the desired temperature and at least one displacement buffer having a $pK_a$ that is at least 2 units less than the pH of the composition at the desired temperature. For the purposes of clarity, where a displacement buffer possesses a plurality of $pK_a$'s, the pH of the solution is not within 1, 1.5 or 2, as the case may be, of each $pK_a$.

Apart from the contribution to pH buffering, the presence of displacement buffers was shown in many cases to have a beneficial effect on the protein stability. For example, in one embodiment, protein activity of a protein in a composition in accordance with the invention retains at least 40% of its activity for at least one week, and preferably at least four weeks at a desired temperature (e.g. ambient temperature or higher), In another embodiment, protein activity of a protein in a composition in accordance with the invention retains at least 50% of its activity for at least one week at the desired temperature, and preferably at least four weeks at a desired temperature (e.g. ambient temperature or higher). In another embodiment, at least 40% and preferably at least 50% protein structural activity of a protein present in a composition according to the invention is retained for at least one week and more preferably for at least 4 weeks at the desired temperature.

In accordance with the present invention the protein composition preferably does not comprise a conventional buffer in a meaningful amount. In other words, the protein composition contains less than a meaningful amount of the conventional buffer. Conventional buffers are typically applied in protein compositions at concentrations 2-200 mM, more typically at 5-50 mM and most typically at about 20 mM concentration. The term "conventional buffer" is therefore defined herein as any chemical species with a $pK_a$ less than one unit but preferably less than 0.5 units away from pH of the composition as measured at the intended temperature range of storage of the composition which possesses a buffering capacity for the protein. The term "less than a meaningful amount" means that the conventional buffer is present in the composition at concentration less than 5 mM, but preferably less than 2 mM.

The invention is applicable to stabilization of a protein throughout its product life including isolation or expression, purification, transport and storage.

Further aspects of the invention include:
  Use of aromatic carboxylate ions to increase the stability of an aqueous composition comprising a protein and an aromatic preservative; and
  A method of increasing the stability of an aqueous composition comprising a protein and an aromatic preservative which comprises adding to the composition aromatic carboxylate ions.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

EXEMPLIFICATION

Example 1

Effect of Benzoate Ion on the Rate of Aggregation in Aqueous Compositions of Human Growth Hormone (hGH) at 40° C. in the Presence of Phenol as a Preservative Formation of high molecular weight species (HMWS) was followed in aqueous solutions of hGH (15 mg/mL) using the following size-exclusion HPLC method: The mobile phase was prepared by mixing 97 parts (v/v) of 63 mM sodium phosphate (pH 7.0) with 3 parts (v/v) of propan-2-ol. The mobile phase was filtered prior to its use.

The liquid chromatograph (Agilent 1100 series) was equipped with a 214 nm detector, guard column and a 7.8×300 mm BioSep SEC-S2000 column. The flow rate was maintained at 0.6 ml/min. 15 µl of aqueous samples of hGH were injected. The percentage of HMS was expressed as the ratio of the total area of all peaks with shorter elution time than the monomeric form of hGH versus the total peak area, ignoring peaks corresponding the excipients. The hGH solutions were incubated at 40° C. and assessed for the presence of HMWS at specific timepoints. In addition, the samples were assessed by eye for signs of visible precipitation. The effect of benzoate anion (in the form of potassium benzoate) was studied on the rate of aggregation in two different background solutions:

Background solution 1: histidine (10 mM), mannitol (264 mM), Poloxamer 188 (3 mg/ml), phenol (30 mM), pH 6.1.
Background solution 2: lactate (100 mM), TRIS (20 mM), Poloxamer 188 (3 mg/ml), phenol (30 mM), pH 6.1.

The rate of HUNS formation at 40° C. is shown in Table 1. It was shown that the presence of 10 mM benzoate anion resulted in lower rate of HMWS formation both in background solution 1 and in background solution 2.

TABLE 1

Effect of formulation components on the rate of formation of high molecular weight species (HMWS) in aqueous compositions of hGH following incubation at 40° C.

| Formulation parameters/components | | HMWS (%) | | |
|---|---|---|---|---|
| Background solution | Benzoate (mM) | T0 | 40° C. (4 weeks) | 40° C. (9 weeks) |
| Background solution 1 | 0 | 1.3 | 9.0 | 22.5 |
| Background solution 1 | 10 | 1.2 | 6.5 | 17.5 |
| Background solution 2 | 0 | 1.2 | 6.1 | 15.0 |
| Background solution 2 | 10 | 1.4 | 4.7 | 10.8 |

Example 2

Effect of Aromatic Carboxylates and Other Compounds on Stability of Uricase 60° C. in the Presence of Phenol and m-Cresol Preservatives Uricase was obtained from Sigma (U0880). The enzyme was formulated at 100 µg/ml. Measurements of enzyme activity were performed on a 96-well plate using an optical assay: 10 µl of the formulation was mixed with 100 enzyme diluent solution (borate buffer 25 mM, pH 8.5) and 50 µL substrate (sodium urate 2 mM). The mixture was equilibrated at room temperature for about 5 min. After 5 min, the following reagents were added in this particular order to each sample (the first reagent must be added at exactly 5 min, the timing of the other reagents addition is less crucial): 50 µl of citrate/phosphate buffer (0.5 M. pH 4.0); 15 µL of TMB (3 mg/mL, dissolved in DMSO) then 15 µL of lactoperoxidase (1 mg/mL, dissolved in water). The resulting solution was mixed thoroughly and absorbance was read at 630 nm using a plate reader. Optical density was calibrated using a range of concentrations of a reference enzyme solution. All measurements were carried out in triplicates and average value was recorded. Stability of enzyme was found in the preliminary experiments to be optimal at pH around 8.0, with minimal effect of ionic strength on the stability. The preservation of the enzyme activity was studied in a background formulation containing 10 mM histidine and 300 mM 1,2-propanediol, adjusted to pH 8. With the exception of control samples, the enzyme solutions contained either phenol (30 mM) or benzyl alcohol (30 mM) as a preservative. The effect of the stabilizing excipients was studied by comparing the stability of uricase in the solution containing the preservative only with that in the solution containing both the preservative and the stabilizing component. The concentration of the additives tested was selected based on their solubility in aqueous solutions.

It was shown Table 2) that the presence of the preservatives (phenol or benzyl alcohol) resulted in impairment of stability of uricase at 60° C. Whilst 78.9% of the original activity of the enzyme was observed following incubation at 60° C. for 6 hours in the absence of the preservatives, the activity recovery was 55.6% in the presence of phenol and 57.7% in the presence of benzyl alcohol. The presence of an aromatic carboxylate as an additional excipient in the preservative-containing compositions resulted in reduction of the destabilizing effect of the preservatives. In contrast the presence of a non-aromatic carbocyclic carboxylate (ions of cyclohexane carboxylic acid) caused an increase in the destabilising effect.

TABLE 2

Effect of formulation components on the stability of uricase at 60° C. in a background composition consisting of histidine (10 mM), and 1,2-Propanediol (300 mM), pH 8.0. Stability is expressed as percentage of activity measured following incubation at 60° C. for 6 hours with respect to the activity measured in a freshly prepared sample.

| | Preservative Activity recovery | |
|---|---|---|
| | Phenol (30 mM) | Benzyl alcohol (30 mM) |
| Sample (with respect to the presence of a preservative and additional additives) | | |
| No preservative, no additive | 78.9% | 78.9% |
| Preservative, no additive | 55.6% | 57.7% |
| Additives tested (all in the presence of preservative) | | |
| Cyclohexane carboxylic acid (20 mM) | 28.5% | 41.9% |
| Mandelic Acid (20 mM) | 68.6% | 85.8% |
| Phthalic acid (10 mM) | 67.8% | 75.8% |
| trans-cinnamic acid (5 mM) | 58.5% | 69.0% |
| Phenylacetic acid (5 mM) | 57.7% | 66.6% |
| Benzoic acid (20 mM) | 67.2% | 79.3% |

Example 3

Effect of Aromatic Carboxylates on Stability of Horseradish Peroxidase (HRP) at 60° C. in the Presence of a Preservative HRP was obtained from Sigma (P8250), The enzyme was formulated at 0.5 mg/ml. Measurements of enzyme activity were performed on a 96-well plate using an optical assay: 20 µl of the formulation was mixed with 180 µl enzyme diluent solution (1.82 mM ABTS, 28 mM hydrogen peroxide in 0.1M sodium phosphate buffer pH 7.0). The resulting solution was mixed thoroughly and absorbance was read at 630 nm using a plate reader after 5 min. Optical density was calibrated using a range of concentrations of a reference enzyme solution. All measurements were carried out in triplicates and average value was recorded. Stability of enzyme was found in the preliminary experiments to be optimal at pH around 7.0 and relatively independent of ionic strength. The preservation of the enzyme activity was studied in background formulations containing 10 mM TRIS and 1,2-propanediol (300 mM) at pH 7.0. With the exception of control solutions, the solutions contained m-cresol (30 mM). The effect of the stabilizing excipients was studied by comparing the stability of HRP in the solution containing the preservative only with that in the solution containing both the preservative and the stabilizing component. The concentration of the additives tested was selected based on their solubility in aqueous solutions.

It was shown (Table 3) that the presence of a selected preservative (m-cresol) resulted in a slight impairment of stability of HRP at 60° C. Whilst 90.2% of the original activity of the enzyme was observed following incubation at 60° C. for 6 hours in the absence of the preservative, the activity recovery was 79.5% in the presence of m-cresol. The presence of an aromatic carboxylate as an additional excipient in the preservative-containing compositions resulted in reduction of the destabilizing effect of the preservatives.

TABLE 3

Effect of formulation components on the stability of HRP at 60° C. in a background composition consisting of TRIS (10 mM), and 1,2-Propanediol (300 mM), pH 7.0. Stability is expressed as percentage of activity measured following incubation at 60° C. for 6 hours with respect to the activity measured in a freshly prepared sample.

| Sample (with respect to the presence of a preservative and additional additives) | m-Cresol as preservative Activity recovery |
|---|---|
| No preservative, no additive | 90.2% |
| Preservative, no additive | 79.5% |
| Additives tested (all in the presence of preservative) | |
| Phenylacetic acid (5 mM) | 97.0% |
| Benzoic acid (20 mM) | 99.3% |

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The invention embraces all combinations of preferred and more preferred groups and suitable and more suitable groups and embodiments of groups recited above.

The invention claimed is:

1. An aqueous pharmaceutical composition comprising a protein; an aromatic preservative selected from the group consisting of phenol, m-cresol and benzyl alcohol, at a molar concentration of 10-60 mM; and aromatic carboxylate ions of a member selected from the group consisting of: benzoic acid, 2-hydroxybenzoic acid, 3-hydroxybenzoic acid, 4-hydroxybenzoic acid, 3,4,5-trihydroxybenzoic acid, 4-hydroxy-3-methoxybenzoic acid, phthalic acid (1,2), isophthalic acid (1,3), terephthalic acid (1,4), 1-naphthoic acid, 2-naphthoic acid, indole-3-acetic acid, phenylacetic acid, 3-phenylpropionic acid, trans-cinnamic acid, cis-cinnamic acid, and mandelic acid;
   wherein the molar concentration of carboxylate ions is 30-100 mM;
   wherein the protein stability is improved upon storage at room temperature for at least 1 month compared to the aqueous composition without the aromatic carboxylate ions; and
   wherein the pH of the composition is at least one unit higher than the pKa of the carboxylate group of the aromatic carboxylate ions.

2. A composition of claim 1 wherein the aromatic carboxylate ions are benzoate ions.

3. A composition of claim 2 wherein the molar concentration of benzoate ions is 30-40 mM.

4. A composition of claim 3 wherein the molar concentration of benzoate ions is 30 mM.

5. A composition of claim 2 wherein the molar concentration of the aromatic preservative is 10-30 mM.

6. A composition of claim 2 wherein the molar concentration of the aromatic preservative is 20-40 mM.

7. A composition of claim 2 wherein the aromatic preservative is present at a concentration that passes the Pharmacopoeia Antimicrobial Effectiveness Test.

8. A composition of claim 2 wherein the benzoate ions are derived from at least 90% ionized benzoic acid.

9. A composition of claim 1 wherein the pH of the composition is at least about 5.2.

10. A composition of claim 9 wherein the pH of the composition is at least about 5.5.

11. A composition of claim 9 wherein the pH of the composition is at least about 6.0.

12. A composition of claim 1 further comprising a buffer selected from the group consisting of Tris(hydroxymethyl)aminomethane (TRIS), glycine, arginine and methionine.

13. A composition of claim 1 wherein the protein is a therapeutic protein for a multi-dose application.

14. A composition of claim 1 wherein the protein is selected from the group consisting of a peptide hormone, growth factor, therapeutic enzyme, vaccine, interferon and a blood factor.

15. A composition of claim 1 further comprising one or more protein stabilizing agents selected from the group consisting of a protease inhibitor, chelating agent, sugar and a detergent.

16. A composition of claim 1 wherein the protein is part of a vaccine containing an inactivated or attenuated virus or a whole cell vaccine.

17. A composition of claim 1 wherein the molar concentration of aromatic carboxylate ions is 30-40 mM.

18. A composition of claim 17 wherein the molar concentration of aromatic carboxylate ions is 30 mM.

19. A composition of claim 1 wherein the molar concentration of the aromatic preservative is 10-30 mM.

20. A composition of claim 1 wherein the molar concentration of the aromatic preservative is 20-40 mM.

21. A composition of claim 1 wherein the aromatic preservative is present at a concentration that passes the Pharmacopoeia Antimicrobial Effectiveness Test.

* * * * *